United States Patent [19]

Rathbone et al.

[11] Patent Number: 4,703,762

[45] Date of Patent: Nov. 3, 1987

[54] BLOOD SAMPLING DEVICE FOR OBTAINING DUAL SAMPLES OF VENOUS BLOOD

[76] Inventors: R. Rodion Rathbone, 1800 Whitney Ave., Hamden, Conn. 06514; Stephen C. Wardlaw, 128 Sunset Hill Dr., Branford, Conn. 06405

[21] Appl. No.: 893,002

[22] Filed: Aug. 4, 1986

[51] Int. Cl.[4] ............................................. A61B 5/00
[52] U.S. Cl. .................................. 128/763; 128/770; 604/403
[58] Field of Search .............................. 128/763–768, 128/770; 604/167, 215, 236–238, 264, 272, 403, 406, 411, 414

[56] References Cited

U.S. PATENT DOCUMENTS

| 2,368,431 | 1/1945 | Smith | 604/403 |
|---|---|---|---|
| 3,648,684 | 3/1972 | Barnuell et al. | 128/764 |
| 3,706,305 | 12/1972 | Berger et al. | 128/764 |
| 3,908,638 | 9/1975 | Porcher et al. | 128/763 |
| 4,020,831 | 5/1977 | Adler | 604/403 |
| 4,050,451 | 9/1977 | Columbus | 128/764 |
| 4,215,700 | 8/1980 | Crouther et al. | 128/763 |
| 4,373,535 | 2/1983 | Martell | 128/765 |
| 4,385,637 | 5/1983 | Akhavi | 128/763 |
| 4,390,016 | 6/1983 | Riess | 604/236 |
| 4,595,021 | 6/1986 | Shimizu et al. | 128/765 |

Primary Examiner—William E. Kamm
Assistant Examiner—Max F. Hindenburg
Attorney, Agent, or Firm—William W. Jones

[57] ABSTRACT

This device is adapted for taking venous blood samples without the aid of any auxiliary negative pressure. Venous blood pressure is the sole force which fills the device with the blood sample. The device includes a flexible plastic tube formed from polyethylene or the like and further includes a blood drawing needle mounted on one end of the tube. A valved closure is disposed at the other end of the tube, the valve being operable to allow passage of air from the tube when the sample is drawn. The valve does not, however, allow the passage of blood from the tube. The tubes may be connected in tandem so as to allow the drawing of two samples with one venipuncture. The first tube can be devoid of an anti-coagulant coating while the second tube can include an anticoagulant coating. In this way, one drawn sample will be anti-coagulated and the other will not.

9 Claims, 6 Drawing Figures

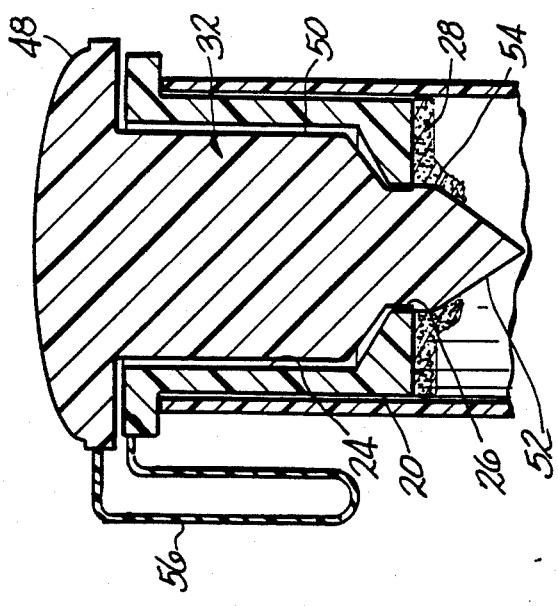
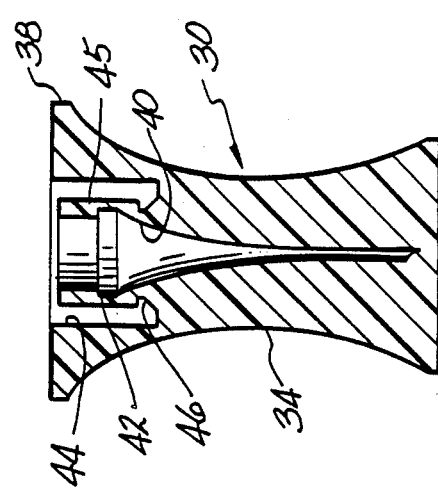
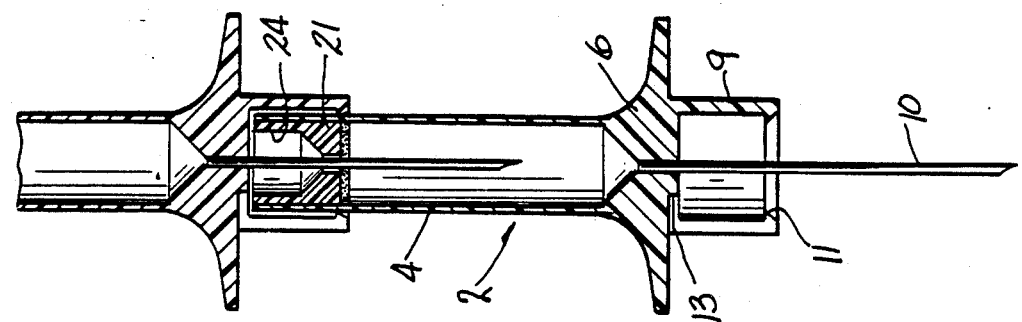
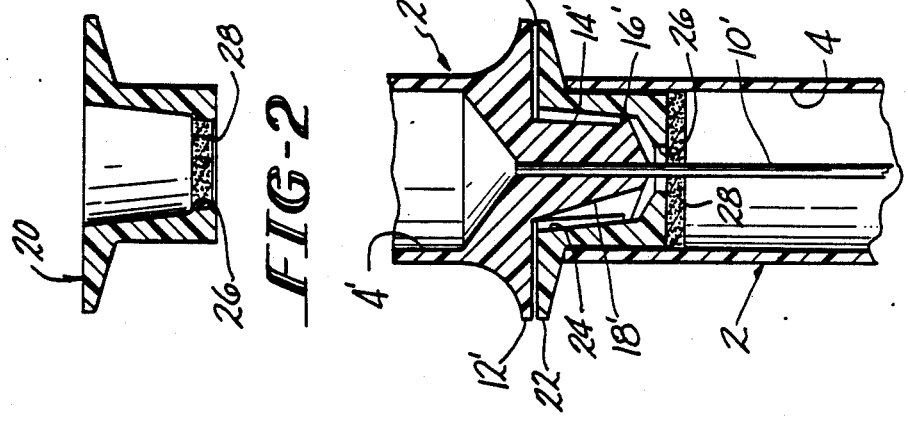
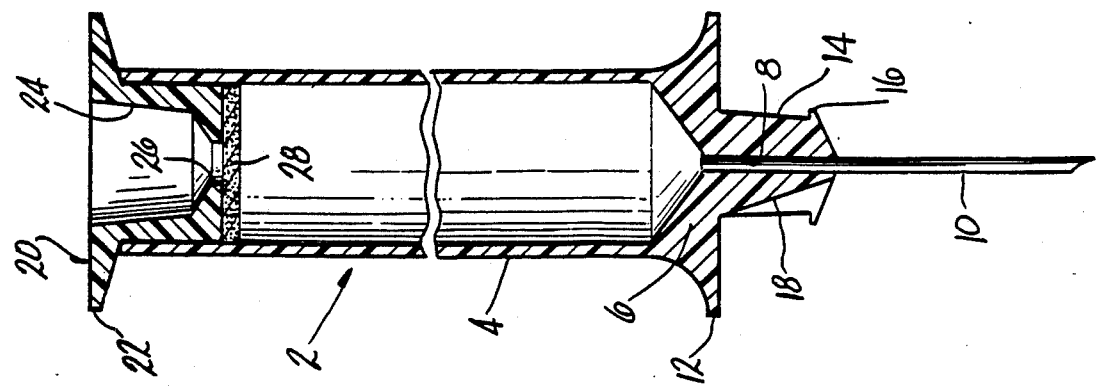

BLOOD SAMPLING DEVICE FOR OBTAINING DUAL SAMPLES OF VENOUS BLOOD

This invention relates to a device for drawing blood samples solely under venous pressure. No auxiliary negative pressure need be used to draw the blood into the device of this invention.

Blood samples may be drawn by means of a number of different procedures and paraphenalia. For example, blood may be drawn using a capillary tube finger stick when only small samples are needed. Larger samples are generally taken with pre-evacuated tubes which operate with needles which penetrate the vein. The contained vacuum within the tube then causes the blood to be drawn quickly into the tube. Illustrative of this manner of drawing blood is the disclosure of U.S. Pat. No. 4,187,861 to B. T. Heffernan.

Another way of drawing blood which is disclosed in the prior art utilizes arterial blood pressure as the force which causes the blood to flow into the collecting device. This type of device uses a collecting tube made from plastic, or the like, a needle at one end of the tube, and an air pressure relief valve at the other end of the tube. The valve is in the form of a non-wetting filter disk which allows passage of air but prevents passage of blood. When the sample is taken, arterial blood pressure forces the blood into the collection tube and air is forced out of the tube via the filter disk. The filter disk is impermeable to blood so that the device will not accept further blood, once filled. This technique is described in U.S. Pat. Nos. 4,266,558; 4,266,559; 4,317,455; and 4,367,754 all to D. S. Akhavi.

Still another procedure for drawing blood disclosed in the prior art involves the use of a flexible plastic collection reservoir which is connected to a collecting tube and which is manually squeezed to create negative pressure for drawing the blood sample. These devices operate in a manner similar to an eye dropper. Such devices are shown in U.S. Pat. Nos. 3,513,829 to Deuschle et al; 4,411,163 to White; and 4,250,893 to White. Conventional syringes may also be used to draw blood.

The devices in the prior art which utilize arterial blood pressure and/or manually created negative pressure to create the flow of blood into the collection reservoir also use the needle or the collection tube as the means for expressing the blood from the device. This means that the collection device cannot be used as a vehicle for certain procedures, as, for example, centrifugation. This also means that the needle is exposed and may accidentally stick someone. It should be noted that the needle may be contaminated with infectious agents.

Devices which are pre-evacuated to take blood samples are uncorked to remove the blood for testing. The blood can be drawn out with a capillary tube, pipette or may be poured out. The blood sample may be centrifuged in the evacuated collection tube, and the centrifuged components can then be drawn out of the tube for analysis.

When some prior art devices are used to draw anticoagulated and non-anticoagulated blood samples for different test procedures, two separate venipunctures must be made, one with an anticoagulant-coated device, and another with a device which does not have an anticoagulant coating. With other prior art devices, the evacuated tubes must be manually changed, which risks dislodging the needle from the veins.

The device of this invention utilizes venous blood pressure, which may be augmented by a tourniquet, to allow the sample to flow into the collection reservoir. The device includes a tubular member, which may be elastomeric, which receives the blood sample. The tubular member is connected to a needle-bearing base which is a relatively rigid material. A valve member is positioned in the tubular member remote from the base. The valve is operable to allow passage of air but block passage of blood. Also included is a needle closing member which takes the form of a contoured body formed from an elastomeric material. The needle is pressed into the needle closing member, and the latter is adapted to interlock with the needle-bearing base of the device. In this manner, the needle is both sealed and safely shielded. Once the needle is sealed, blood or blood components can be removed from the device via the valved end of the device. The needle closing member is formed so as to fit snugly into the bottom of a test tube in which the device is stored. This adapts the device for in-situ centrifugation of the blood sample. The device of this invention is adapted to be used in a tandem arrangement wherein multiple blood samples can be drawn. The tandem components can be differentiated so that one sample can be whole blood and the other can be anticoagulated blood. To form the tandem arrangement, one of the devices is connected to another by passing the needle of the one through a receptor end of the other. In one embodiment of the device, the needle of one device is passed through the valve of the other. In an alternative embodiment, the needle passes through a self-sealing membrane in the other device. The interfitting ends of the two devices are formed to provide a stable mating connection between the devices.

It is, therefore, an object of this invention to provide a blood sampling device which can utilize venous blood pressure as the sole force which causes blood to flow into the device.

It is a further object of this invention to provide a blood sampling device of the character described which includes a valve which allows passage of air from the device during drawing of the blood sample but does not allow passage of blood.

It is a further object of this invention to provide a blood sampling device of the character described, which includes separable units which can be joined to form a single unit for the purposes of obtaining the blood sample, and in which the valves serve to allow filling of each unit, as well as allowing retrieval of the collected specimen.

It is yet another object of this invention to provide a blood sampling device of the character described which is adapted to be connected in tandem to another similar device to allow drawing of multiple blood samples with a single venipuncture.

It is another object of this invention to provide a blood sampling device of the character described which is adapted to be thus connected by inserting the needle of one device into another of the devices.

It is an additional object of this invention to provide a blood sampling device of the character described which has a needle plug adapted to be locked to the remainder of the device and which adapts the device for in-situ centrifugation of the blood sample.

These and other objects and advantages of the device of this invention will become more readily apparent from the following detailed description of preferred embodiments of the invention when taken in conjunction with the accompanying drawings, in which:

FIG. 1 is an axial sectional view of a preferred embodiment of a device formed in accordance with this invention;

FIG. 2 is an axial sectional view of a modified form of the valved end closure used in the device;

FIG. 3 is a fragmented axial sectional view of portions of two of the devices showing the manner in which they are connected in tandem for obtaining two separate blood samples with only a single venipuncture;

FIG. 4 is a fragmented axial sectional view showing two of the devices connected in tandem with a modified form of interlocking end;

FIG. 5 is a fragmented sectional view of the needle closure used to close the needle end of the embodiments of the device shown in FIGS. 1 and 4; and FIG. 6 is a fragmented sectional view of the valved end of the device showing a closure plug in place which ruptures the valve while sealing the valved end of this device after taking a blood sample.

Referring now to the drawings, there is shown in FIG. 1 a preferred embodiment of a device, denoted generally by the numeral 2, which is formed in accordance with this invention. The device 2 includes a tubular reservoir portion 4, which is preferably molded from a plastic such as polypropylene, or the like. The reservoir portion 4 has an integral basal part 6 which includes an axial passage 8 in which a venipuncture cannula, or needle, 10 is mounted. A radial flange 12 is formed on the basal part 6 about a central boss 14, which depends downwardly from the flange 12. A locking rib 16 is formed on the lower edge of the boss 14. An air vent slot 18 extends axially of the boss 14 along the outer side thereof. An air venting plug 20 is telescoped into the distal end of the device 2 at the opposite end thereof from the needle 10. The plug 20 includes a radial flange 22 which corresponds in size to the basal flange 12, and a central well 24. The well 24 includes an axial passage 26. The plug 20 is formed from an elastomeric material such as polypropylene, or the like. A wafer 28 of an air permeable, blood impermeable material is mounted on the inner end surface of the plug 20. The wafer 28 forms an air venting valve which allows exhaustion of air from the interior of the reservoir portion 4 as blood is drawn into the portion 4. The valve 28 may be made from sintered polyolefin spheres, or hydrophobic filter paper, or the like.

FIG. 2 shows a variation of the plug 20 wherein the passage 26 is radially enlarged and the valve 28 is contained within the passage 26.

As shown in FIG. 3, two of the devices shown in FIG. 1 can be connected in tandem so as to allow drawing of two separate blood samples with only one venipuncture. In referring to the two tandem devices, like references numerals will be used to identify like components of each device but prime numerals will be used to identify the second of the two devices. To thus connect the devices in tandem, the needle 10' of one device 2' is inserted through the valve wafer 28 of the other device 2, whereby the needle 10' enters the reservoir portion 4 of the device 2. The boss 14' thus enters the well 24 until the rib 16' frictionally engages the wall of the well 24. The rib 16', in this manner, serves to limit the extent to which the boss 14' can enter the well 24 so as to ensure that an air gap G will be maintained between the flanges 12' and 22. The diameter of the needle 10' is substantially smaller than the diameter of the passage 26 so as to ensure that air can pass from the reservoir 4 through the valve 28 into the well 24 outwardly of the boss 14'. The vent slot 18' provides a passage for air from the well 24 to the gap G where the expelled air is vented to the surrounding atmosphere. Once the reservoir 4 is filled with blood, further blood drawn passes through the needle 10' into the reservoir 4' until the latter is also filled with blood. In this way, two separate blood samples can be drawn with a single venipuncture. The second device 2' can have an anticoagulant applied to the interior of the reservoir so that the blood contained in the second device 2' will be anticoagulated, while the blood contained in the first device 2 will not be anticoagulated. Cooperation between the boss 14' and the well 24, as well as between the flanges 12' and 22, provides a stable connection which will not unduly damage the valve 28. After the multiple samples are taken, the device 2 and 2' can be disconnected simply by pulling the boss 14', rib 16' and needle 10' free of the well 24 and valve 26 respectively. Once separated, the two devices are closed by applying a needle closure, denoted generally by the numeral 30 and shown in FIG. 5, to the needle end of the device and by inserting a cap, denoted generally by the numeral 32 and shown in FIG. 6, into the plug end of the device.

The needle closure 30 is made from a relatively soft elastomeric material and includes a trunk part 34, a base 36 and an upper flange 38. A blind bore 40 is formed in the closure 30 extending from the flange 38 toward the base 36. The bore 40 preferably tapers to a point as it approaches the base 36. A locking groove 42 is formed in the side wall of the bore 40. Preferably, a coaxial annular recess 44 is formed in the closure 30 surrounding the bore 40. The recess 44 includes a locking slot 46 formed in its inner wall.

The cap 32 includes a radial flange 48 and a control cylindrical part 50 similar in shape to boss 14, which is received in the well 24 of the plug 20. The cap 32 also includes a punch 52, which passes through the passage 26 and ruptures the valve 28 to allow easy removal of blood aliquots from the device for performance of tests on the blood. The punch 52 includes a basal protrusion 54, which frictionates with the passage 26 to retain the cap 32 in place. If desired, the cap 32 may include an integral cord 56 which interconnects the plug 20 and the cap 32; the two being co-molded in the connected form shown in FIG. 6.

In use, after a blood sample or samples have been taken, the devices are separated and a needle closure 30 is pressed over the needle 10 on each device until the rib 16 on the boss 14 interlocks with the groove 42, thus locking the closure 30 to the device 2. The cap 32 is then pressed into the well 24 in the plug 20 to close the opposite end of the device 2. To withdraw aliquots for testing, the cap 32 is withdrawn, and capillary tubes or pipettes are inserted into the device through the ruptured valve 28. After the necessary samples are taken from the device, the cap 32 can be replaced and the device safely discarded.

FIG. 4 shows an alternative embodiment of a tandem interlock for two of the devices. The basal part 6 of each device is formed with an annular projection 9 which includes a locking rib 11 formed on the interior thereof. A vent slot 13 is provided in the projection 9. The projection 9 is sized so as to snugly telescope over the exterior of the reservoir portion 4 of the device 2, as shown in FIG. 4. The plug 21 is formed without a flange to allow the snug interfit between the tandem devices. When the devices are thus interlocked, the slot 13 allows air to escape from the front device as the blood enters the front device. After the samples are drawn, the devices are disconnected, and the closures 30 are applied to the needles 10. The annular projection 9 fits into the recess 44 and the rib 11 interlocks with the slot 46 to secure the closure 30 to the device 2. The cap 32 is then inserted into the well 24 in the plug 21.

It will be readily appreciated that the device of this invention will be less traumatic to use in that multiple blood samples can be taken with a single venipuncture. The devices, when connected in tandem, can be used to draw both anticoagulated and non-anticoagulated blood samples with a single venipuncture and without changing blood collection tubes. This is accomplished by including an anticoagulant in the second of the tandem devices, while deleting the anticoagulant from the first of the tandem devices. A stable connection is provided between the tandem devices while ensuring that air flow from the first of the tandem will be vented from the blood reservoir as blood flows thereinto. The devices can also be used to draw single blood samples using venous blood pressure as the sole blood movement force.

Since many changes and variations of the disclosed embodiments of the device may be made without departing from the inventive concept, it is not intended to limit the invention otherwise than as required by the appended claims.

What is claimed is:

1. A device which uses venous blood pressure for drawing blood samples, said device comprising:
    (a) a first member including:
        (i) a first tubular reservoir portion for receiving a blood sample, a venapuncture needle mounted on one end of said reservoir portion, and valve means closing the other end of said reservoir portion, said valve means being operable to allow venting of air from said reservoir portion while preventing passage of blood from said reservoir portion;
        (ii) means forming a boss about said needle at said one end of said reservoir portion, said boss having an air vent passage therein which passage does not enter said reservoir portion;
        (iii) means forming a bore in said other end of said reservoir portion outwardly of said valve means; and
    (B) a second member including a reservoir; a needle; a valve; a boss with an air vent passage; and a bore, said second member being substantially identical in construction with said first member, the needle of said second member extending into said reservoir portion of said first member, and the boss of said second member including means engaging said first member to securely connect said second member to said first member in tandem fashion whereby dual blood samples can be drawn with the device from a single venapuncture.

2. The device of claim 1 wherein the reservoir of said second member has an interior anticoagulant coating and the reservoir portion of said first member has no interior anticoagulant coating.

3. The device of claim 1 wherein said boss of each member is a solid projection having a longitudinal slot forming said vent passage, said projection of said second member being telescopingly received in said bore of said first member to connect the two members together.

4. The device of claim 1 wherein said boss of each member is an annular projection having a longitudinal slot forming said vent passage, said projection of said second member telescoping over and frictionally engaging an outer surface of said first member to connect the two members together.

5. The device of claim 1 further comprising a cap for insertion into said bore to seal the other end of said members after blood samples have been drawn and said members have been disconnected from each other.

6. The device of claim 5 wherein said cap has a punch portion for piercing said valve.

7. The device of claim 5 wherein said cap is integrally connected to said reservoir portion by means of a tether.

8. The device of claim 1 wherein said valve means is formed on a plug which is telescopingly received in the other end of said reservoir portion.

9. The device of claim 8 wherein said bore is formed in said plug.

* * * * *